(12) United States Patent  
Sen et al.

(10) Patent No.: US 8,674,150 B2
(45) Date of Patent: Mar. 18, 2014

(54) ONE-STEP CATALYTIC CONVERSION OF BIOMASS-DERIVED CARBOHYDRATES TO LIQUID FUELS

(75) Inventors: Ayusman Sen, State College, PA (US); Weiran Yang, State College, PA (US)

(73) Assignee: Penn State Research Foundation, University Park, PA (US)

( * ) Notice: Subject to any disclaimer, the term of this patent is extended or adjusted under 35 U.S.C. 154(b) by 354 days.

(21) Appl. No.: 12/930,602

(22) Filed: Jan. 11, 2011

(65) Prior Publication Data

US 2011/0282079 A1 Nov. 17, 2011

Related U.S. Application Data

(63) Continuation-in-part of application No. 12/455,816, filed on Jun. 5, 2009.

(51) Int. Cl.
*C07C 9/00* (2006.01)

(52) U.S. Cl.
USPC .......................................................... 585/14

(58) Field of Classification Search
USPC .......................................................... 585/14
See application file for complete search history.

(56) References Cited

U.S. PATENT DOCUMENTS

| | | | |
|---|---|---|---|
| 4,025,356 A | 5/1977 | Nyman | |
| 4,664,717 A | 5/1987 | Young | |
| 5,536,325 A | 7/1996 | Brink | |
| 6,423,145 B1 | 7/2002 | Nguyen | |
| 2003/0199049 A1 | 10/2003 | Nguyen | |
| 2007/0190620 A1 | 8/2007 | Mueller | |
| 2007/0225383 A1 | 9/2007 | Cortright | |
| 2008/0033188 A1 | 2/2008 | Dumesic | |

OTHER PUBLICATIONS

Campbell et al, The End of Cheap Oil, Scientific American Mar. 1998, pp. 78-84.
Klass, Biomass for renewable energy, fuels and chemical, pp. 10-19, (1998).
Pimentel, Ethanol Fuels: Energy Balance, Economics, and Environmental Impacts are Negative, Natural Resources Research, vol. 12, No. 2, Jun. 2003, pp. 127-137.
Roman-Leshkov et al, Production of dimethylfuran for liquid fuels frombiomass-derived carbohydrates, Nature, Jun. 2007, pp. 982-986.
Zhao et al, Metal Chlorides in Ionic Liquid Solvents Convert Sugars to5-Hydrozymethylfurfural, Science 316, 1597 (2007).
Yong et al, Efficient Catalytic System for the Selective Production of 5-Hydroxymethylfurtural from Glucose and Fructose, Angew. Chem. Int. Ed. 2008, 47, 9345-9348.
Binder et al, Simple Chemical Transformation of Lignocellulosic Biomassino Furans for Fuels and Chemicals, J. Am. Chem. Soc. 2009, 131, 1979-1985 9 1979.

(Continued)

*Primary Examiner* — Andrew D Kosar
*Assistant Examiner* — Raymond Covington
(74) *Attorney, Agent, or Firm* — Law Offices John A. Parrish

(57) ABSTRACT

The invention relates to a method for manufacture of hydrocarbon fuels and oxygenated hydrocarbon fuels such as alkyl substituted tetrahydrofurans such as 2,5-dimethyltetrahydrofuran, 2-methyltetrahydrofuran, 5-methylfurfural and mixtures thereof. The method generally entails forming a mixture of reactants that includes carbonaceous material, water, a metal catalyst and an acid reacting that mixture in the presence of hydrogen. The reaction is performed at a temperature and for a time sufficient to produce a furan type hydrocarbon fuel. The process may be adapted to provide continuous manufacture of hydrocarbon fuels such as a furan type fuel.

15 Claims, 1 Drawing Sheet

(56) References Cited

OTHER PUBLICATIONS

Huber, et al., Production of Liquid Alkanes by Aqueous-Phase Processing of Biomass-Derived Carbohydrates, Science 308, 1446 (2005).

Mascal et al, Direct, High-Yield Conversion of Cellulose into Biofuel, Angew. Chem. Int. Ed. 2008, 47, 7924-7926.

Chundawat et al, Effect of Particle Size Based Separation of Milled Corn Stover on AFEX Pretreatment and Enzymatic Digestibility, Biotectnology and Bioengineering, vol. 96, No. 2, Published online Aug. 10, 2006.

Poster Paper: A Research Roadmap for Making Lignocellulosic Biofuels a Practical Reality, Jun. 2007.

Kunkes, et al., Catalytic Conversion of Biomass to Monofunctional Hydrocarbons and Targeted Liquid-Fuel Classes, Science 322, 417 (2008).

Ragauskas, et al., The Path Forward for Biofuels and Biomaterials, Science 311, 484 (2006).

US 8,674,150 B2

ONE-STEP CATALYTIC CONVERSION OF BIOMASS-DERIVED CARBOHYDRATES TO LIQUID FUELS

This application is a continuation in part of pending U.S. patent application Ser. No. 12/455,816 filed Jun. 5, 2009 and claims priority to U.S. Provisional Patent Application 60/129,160 filed Jun. 6, 2008.

This invention was made with government support under Grant No. DE-FG02-84ER13295, awarded by Department of Energy (DOE). The Government has certain rights in the invention.

FIELD OF THE INVENTION

The invention generally relates to manufacture of liquid fuels. More particularly, the invention relates to manufacture of liquid fuels from biomass-derived materials such as monosaccharides and polysaccharides.

BACKGROUND OF THE INVENTION

Production of renewable liquid fuels directly from biomass resources is of great importance in view of the present high consumption of fossil fuels. Today, about three quarters of the world's energy is provided by fossil fuels such as coal, oil, and natural gas. Fossil fuels, however, are nonrenewable resources. Diminishing reserves of fossil fuels and growing concerns about global warming call for sustainable sources of energy such as renewable liquid fuels.

The increasing cost of fossil fuels and the concerns about their environmental impact are accelerating the transition to a biomass-based economy. While fuel production from biomass has gained significant attention, the use of renewable resources in the production of chemicals is also very important. Typically, chemical intermediates have much greater utility than fuels since they may be transformed into solvents, polymers, and specialty chemicals for which fossil fuels have traditionally been used.

A known method for producing liquid fuels from biomass entails fermentation of sugars to produce ethanol. Ethanol, however, is not a good candidate for a liquid fuel due to its low energy density (23 MJ/L), high volatility (BP 78° C.), and high solubility in water (fully miscible). Liquid fuel candidates such as 2,5-dimethylfuran (DMF) and 2,5-dimethyltetrahydrofuran (DMTHF) which can be produced from renewable biomass therefore have gained interest.

It is known to use a two-step synthesis of 2,5-dimethylfuran (DMF) via 5-hydroxymethylfurfural (HMF) produced by dehydration of fructose. However, the application of this two-step synthesis is limited due to low yield and complicated separations. Moreover, a typical method for manufacture of HMF from cellulose entails either use of aqueous acid hydrolysis at high temperatures and pressures (250-400° C., 10 MPa) at less than 30% yield or use of expensive ionic liquid as solvent.

5-methylfurfural is a useful intermediate for production of pharmaceuticals, agriculture chemicals, perfumes and the like. Large-scale production of 5-methylfurfural employs 5-methylfuran, N,N dimethylformamide and phosphorus oxychloride or phosgene. During manufacture of 5-methylfurfural, a significant excess of poisonous phosphorus oxychloride and N,N-dimethylformamide are used.

Although methods for manufacture of biomass derived liquid fuels are known, these methods have numerous disadvantages as discussed above. A need therefore exists for a method of generating renewable liquid fuels that addresses the disadvantages of the prior art.

SUMMARY OF THE INVENTION

Figure 1:
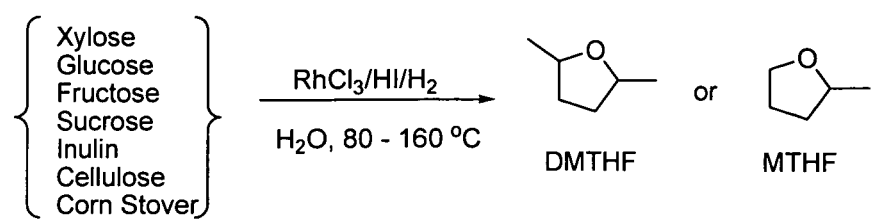
FIG. 1 shows single step conversion of various biomass derived carbohydrates and cellulosic biomass into tetrahydrofuran type liquid fuels.
Figure 2:
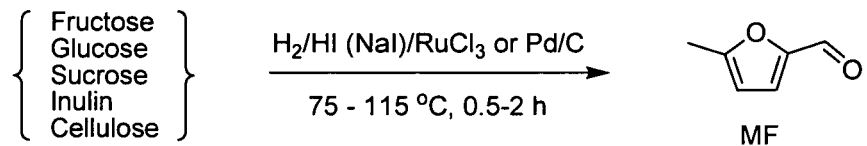
FIG. 2 shows single step conversion of various biomass derived carbohydrates and cellulosic biomass into 5-Methylfurfural.

In a first aspect, the invention relates to single step catalytic conversion of lignocellulosic biomasses as well as single step conversion of biomass-derived carbohydrates into tetrahydrofuran type compounds for use as fuels. Examples of these fuels include but are not limited to 2,5-dimethyltetrahydrofuran (DMTHF), 2-methyltetrahydrofuran (MTHF) and tetrahydrofuran derivatives such as 2,5 dimethylfuran, 2-ethyltetrahydrofuran, 2-methyltetrahydropyan, tetrahydro-5-methylfuran-2-methanol, tetrahydro-5-methylfuran-2-carbaldehyde, 2-methylcyclopentanone and 5-methylfurfural.

Single step conversion of lignocellulosic biomass may be performed with high yield. Conversion may be performed by use of an acid such as HI optionally with an alkali halide salt such as NaCl, NaI and mixtures thereof; HCl optionally with an alkali halide salt such as NaCl, NaI and mixtures thereof; HBr optionally with an alkali halide salt such as NaCl, and $H_2SO_4$ optionally with an alkali halide salt such as any one or more of NaCl, NaI and mixtures thereof. Preferably the acid is HI.

Single step conversion of ligno cellulosic biomass may be performed in the presence of a metal catalyst such as supported Rh, Ru, Pd, Ni, Ir, Cr, Co, and their salts, Pd/C, $RhCl_3$ and mixtures thereof; unsupported Rh, Ru, Pd, Ni, Ir, Cr, Co, and their salts, Pd/C, $RhCl_3$ and mixtures thereof, preferably $RhCl_3.xH_2O$, Pd/C and mixtures thereof. Conversion may be performed under $H_2$ at a pressure of about 30 PSI to about 1000 PSI, preferably about 100 PSI to about 500 PSI, more preferably about 300 PSI, at about 25° C. to about 200° C., preferably about 80° C. to about 160° C., for about 1 h to about 44 h, preferably about 3 h to about 16 h.

Starting materials that may be used in the single step conversion of biomass derived carbohydrates include but not limited to hexoses such as glucose, fructose, mannose, galactose, sorbose, and mixtures thereof; pentoses such as xylose, ribose, arabinose, and mixtures thereof; any one or more of di-saccharides, oligo-saccharides and polysaccharides such as sucrose, cellobiose, amylose, inulin, starch, cellulose, hemi-cellulose, xylan, and mixtures thereof. Where pentose is employed in the single-step conversion process, a five carbon compound is produced with high selectivity.

The single step conversion process may be used to convert a wide variety of biomass feedstock, including but not limited to raw lignocellulosic biomass such as plant leaves, roots, seeds, and stalks, corn stalks, straw, seed hulls, sugarcane leavings, jatropha, switchgrass, corn stover, nutshells and mixtures thereof; wood materials such as wood, bark, sawdust, timber slash, mill scrap and mixtures thereof; municipal waste such as waste paper, yard clippings and mixtures thereof; and energy crops such as poplars, willows, switch grass, alfalfa, prairie bluestem, corn, soybean and mixtures thereof.

In a second aspect, the invention relates to a method for manufacture of hydrocarbon fuels and oxygenated hydrocarbon fuels such as alkyl substituted tetrahydrofurans such as 2,5-dimethyltetrahydrofuran, 2-methyltetrahydrofuran and mixtures thereof. The method entails forming a mixture of two or more reactants that includes a carbonaceous material such as hexoses, pentoses, polysaccharides, lignocelluloses and mixtures thereof, water, a metal catalyst and an acid. The mixture is reacted in the presence of hydrogen. The reaction may be performed at about 25° C. to about 200° C. for a time sufficient to produce a furan type hydrocarbon fuel. The hydrogen may be employed at a pressure of about 30 PSI to about 1000 PSI. Where the carbonaceous material is a hexose, the hydrogen pressure may be about 200 PSI to about 500 PSI and the hexose may be any of glucose, fructose, mannose, galactose, sorbose and mixtures thereof, preferably fructose. The metal catalyst may be any one or more of supported Rh, Ru, Pd, Ni, Ir, Cr, Co, unsupported Rh, Ru, Pd, Ni, Ir, Cr, Co, salts of any of Rh, Ru, Pd, Ni, Ir, Cr, Co, mixtures thereof and the acid may be any one or more of HI, HCl, HBr, $H_2SO_4$ and acids such as phosphotungstic acid and mixtures thereof. In this aspect, the metal catalyst preferably is $RhCl_3 \cdot xH_2O$ and the mixture may further include an organic solvent such as halo benzene such as $C_6H_5Cl$.

In a third aspect, the invention relates to manufacture of furan derivative fuel from biomass derived carbohydrates. In this aspect, the method entails forming a mixture of reactants that includes a carbonaceous material such as fructose, glucose, inulin, sucrose, cellulose, xylose and mixtures thereof, a metal catalyst, an acid, and an organic solvent. The mixture of reactants is treated under hydrogen at an elevated temperature for a period of about 4 h to about 20 h to produce a furan derivative fuel.

In a fourth aspect, the invention relates to a method of conversion of a lignocellulose to a furan type fuel. In this aspect, the method entails forming a mixture that includes a lignocellulose, metal catalyst, water, acid, alkali halide salt and aromatic solvent. The mixture is reacted in hydrogen at a pressure of about 30 PSI to about 500 PSI at a temperature of about 80° C. to about 200° C. to produce a furan fuel. The lignocellulose may be any of plant leaves, roots, seeds, corn stalks, straw, seed hulls, sugarcane leavings, jatropha, switchgrass, corn stover, nutshells, wood, sawdust, poplars, willows, switch grass, alfalfa, prairie bluestem, corn, corn stover and mixtures thereof. The lignocellulose preferably is corn stover, the catalyst preferably is $RhCl_3 \cdot xH_2O$, the acid preferably is HCl, the salt preferably is NaI, the solvent preferably is benzene, the hydrogen preferably is at a pressure of about 300 PSI and the temperature preferably is about 160° C.

In a fifth aspect, the invention relates to a method of continuous manufacture of a furan type fuel. In this aspect, the invention entails forming a reaction mixture of a carbonaceous material, acid, water and metal catalyst, and then reacting the mixture under hydrogen at elevated temperature for a time sufficient to generate a reaction product that includes a furan type fuel. The reaction product is combined with an aromatic solvent to form a solvent blend having the furan type fuel. The solvent blend having the fuel therein is removed from the reaction product, and an additional amount of carbonaceous material may be added to form a second reaction mixture that may be employed in the manner above with respect to use of the first mixture to generate furan type fuel. These steps may be repeated.

In a sixth aspect, the invention relates to direct catalytic synthesis of 5-methylfurfural from biomass-derived carbohydrates using a multifunctional catalyst and a biphasic reaction system. The catalyst system is robust and can be recycled.

Where the carbohydrate starting material is fructose, about 68% of 5-methylfurfural can be obtained in about 0.5 h at about 90° C.

In another aspect, the invention relates to a method for manufacture of 5-methylfurfural. The method entails forming a reactant mixture that includes a carbohydrate such as hexoses, pentoses, polysaccharides and mixtures thereof, water, an aromatic solvent and a catalyst such as $RhCl_3 \cdot xH_2O$ (Rh 38.5-45.5%), Pd/C, Ru/C, $RuCl_3$, Rh/C, $NiI_3$, $PdI_3$, $RhI_3$ and $IrCl_3 \cdot xH_2O$ and mixtures thereof, an acid such as HI, HCl, HBr, $H_2SO_4$ and mixtures thereof, and reacting the mixture under hydrogen pressure of about 30 PSI to about 1000 PSI at about 25° C. to about 200° C. for about 0.5 h to about 44 h to form 5-methylfurfural product. In a preferred aspect, the carbohydrate may be a hexose or fructose, the acid may be HI and the catalyst may be any one or more of $RuCl_3$ and Pd/C. The aromatic solvent may be benzene, toluene, chlorobenzene and mixtures thereof. In another preferred aspect, manufacture of 5-methylfurfural entails forming a reaction mixture of fructose, HI, catalyst, water and benzene, and reacting the mixture under hydrogen pressure of about 300 PSI at about 75° C. to about 90° C. for about 0.5 h to about 2 h to produce 5-methylfurfural where the catalyst is $RuCl_3$ or Pd/C. In another aspect, manufacture of 5-methylfurfural entails use of carbohydrate such as inulin, sucrose, glucose, cellulose or mixtures thereof, HI, $RuCl_3$ catalyst, water and benzene, and reacting the mixture under hydrogen pressure of about 300 PSI at about 75° C. to about 90° C. for about 2 h to produce 5-methylfurfural.

In yet another aspect, the invention relates to method for continuous manufacture of 5-methylfurfural. The method entails step 1: forming a reactant mixture that includes a carbohydrate such as hexoses, pentoses, polysaccharides, and mixtures thereof, water, an aromatic solvent and a catalyst such as $RhCl_3 \cdot xH_2O$ (Rh 38.5-45.5%), Pd/C, Ru/C, $RuCl_3$, Rh/C, $NiI_3$, $PdI_3$, $RhI_3$ and $IrCl_3 \cdot xH_2O$ or mixtures thereof, an acid such as HI, HCl, HBr, $H_2SO_4$ and mixtures thereof, step 2: reacting the mixture under hydrogen pressure of about 30 PSI to about 1000 PSI at about 25° C. to about 200° C. for about 0.5 h to about 44 h to form a reaction product having 5-methylfurfural, and step 3: separating the 5-methylfurfural from the reaction product to form an aqueous portion having catalyst and acid, combining the aqueous portion with additional carbohydrate and aromatic solvent, and repeating steps 2 and 3.

Having summarized the invention, the invention is described in further detail below by reference to the following detailed description and non-limiting examples.

DETAILED DESCRIPTION OF THE INVENTION

Materials.

Ruthenium(III) chloride hydrate is available from Pressure Chemical, Inc.

5% palladium on carbon (Pd/C) is available from Johnson Matthey.

Catalysts such as $RhCl_3 \cdot xH_2O$ (Rh 38.5-45.5%), Pd/C, Ru/C, $RuCl_3$, Rh/C, $NiI_3$, $PdI_3$, $RhI_3$, and $IrCl_3 \cdot xH_2O$ are available from sources such as Alfa Aesar.

5-chloromethylfurfural is available from Alchem Laboratories.

Carbohydrates such as glucose, fructose, sucrose, inulin, cellulose and xylose are available from Sigma-Aldrich or Alfa Aesar.

Cellulose in the form of powder that has an average particle size of about 20 micron is available from Sigma-Aldrich.

High-pressure hydrogen is available from GT&S, Inc. and is used without further purification.

Isotopically enriched chemicals such as $C_6D_6$ and $D_2O$ are available from Cambridge Isotope Laboratories and may be used without further purification.

Feedstock:

A variety of carbohydrates may be used as feedstocks in the present method. For example, feedstocks may include but are not limited to hexoses such as glucose, fructose, mannose, galactose, sorbose, and mixtures thereof; pentoses such as xylose, ribose, arabinose, and mixtures thereof; any one or more of di-saccharides, oligo-saccharides, and polysaccharides such as sucrose, cellubiose, amylose, inulin, starch, cellulose, hemi-cellulose, xylan, and mixtures thereof.

As used herein, the term "biomass" refers to organic materials produced by plants such as leaves, roots, seeds, and stalks without limitation. Common sources of biomass include but are not limited to: (1) agricultural wastes such as corn stalks, straw, seed hulls, sugarcane leavings, nutshells and mixtures thereof, (2) wood materials such as wood, bark, sawdust, timber slash, mill scrap and mixtures thereof; (3) municipal waste such as waste paper, yard clippings and mixtures thereof; and (4) energy crops such as poplars, willows, switch grass, alfalfa, prairie bluestem, corn, soybean and mixtures thereof.

Catalyst Selection

Catalysts may be selected on the basis of function as effective stable hydrogenation catalysts under the acidic conditions employed. Catalysts that may be employed include but are not limited to supported Ru, Pd, Ni, Ir, Cr, Co, and their salts and mixtures thereof; unsupported Rh, Ru, Pd, Ni, Ir, Cr, Co and their salts and mixtures thereof, $RhCl_3.xH_2O$ (Rh 38.5-45.5%) as well as metal catalysts such as Pd/C, Ru/C, $RuCl_3$, Rh/C, $NiI_3$, $PdI_3$, $RhI_3$, and $IrCl_3.xH_2O$.

Conversion

Conversion of carbohydrates, as shown in FIG. 1, entails reacting an aqueous mixture of starting materials that includes a carbohydrate such as any one or more of hexoses, pentoses, polysaccharides, lignocelluloses and mixtures thereof, acid and catalyst in $H_2$. Hexoses that may be used include but not limited to glucose, fructose, mannose, galactose, sorbose and mixtures thereof; pentoses that may be used include but not limited to xylose, ribose, arabinose and mixtures thereof; polysaccharides that may be employed include not limited to sucrose, inulin, cellulose, cellobiose, hemi-cellulose, xylan, and mixtures thereof; lignocelluloses that may be used include but not limited to corn stover, plant leaves, roots, seeds, corn stalks, straw, seed hulls, sugarcane leavings, jatropha, switchgrass, corn stover, nutshells, wood, sawdust, poplars, willows, switch grass, alfalfa, prairie bluestem, corn, and mixtures thereof. The aqueous mixture is reacted under hydrogen at about 80° C. to about 160° C. for about 2 h to about 44 h to yield tetrahydrofuran type fuels such as DMTHF, MTHF and mixtures thereof. The acids that may be employed include but are not limited to HI optionally with an alkali halide salt such as NaCl, NaI and mixtures thereof; HCl optionally with an alkali halide salt such as NaCl, NaI and mixtures thereof; HBr optionally with alkali halide salt such as NaCl; $H_2SO_4$ optionally with an alkali halide salt such as NaCl; NaI and mixtures thereof, as well as mixtures of these acids.

An organic solvent may be added to the aqueous mixture prior to reacting the starting materials as described above. Examples of solvents that may be employed include but are not limited to aromatics such as benzene, toluene, chlorobenzene and mixtures thereof; alkanes such as isooctane, decane and mixtures thereof as well as mixtures of aromatics and alkanes. The organic solvents may be added to the aqueous mixture in amounts of about 10 wt. % to about 200 wt. %, preferably about 50 wt. % to about 100 wt. % based on the weight of aqueous mixture.

Analysis Methods.

Products may be analyzed by 1H NMR spectroscopy (Bruker Avance-360 spectrometer equipped with a quad-nuclear probe operating at 360.13 MHz), GC (HP Hewlett Packard-5890 series II with a FID detector; 95% dimethyl/5% diphenyl-polysiloxane column) and GC-MS (Waters GC-TOF with Agilent 6890 GC; 20 meter 150 mm I.D., 0.15 um 95% dimethyl/5% diphenyl-polysiloxane film column; 70 eV electron ionization). The 1H NMR spectra and the GC retention times of the products are also compared with commercially available samples such as from Sigma-Aldrich.

Methods Used for Gas Chromatography "GC" and Gas Chromatography-Mass Spectrometry "GC-MS" Analysis.

The method used for GC analysis is as follows: The initial oven temperature is 40° C.; then temperature is ramped at 3° C./min until 100° C. is reached; after that, temperature is ramped at 10° C./min until 200° C. is reached and held for 5 min. The method used for GC-MS analysis is as follows: The initial oven temperature is 40° C. and is held for 1 min; the program rate is 15° C./min until 290° C. is reached and is held for 7 min; the total time elapsed is 25 min. The injector temperature is 290° C. with a split of 20/1. The helium flow rate is 0.5 ml/min. The temperature of transfer line is 220° C. The mass scan is 35-650 Da/sec.

Quantification Methods.

Yields of products are determined from 1H NMR spectra and GC analysis of the organic layer by using nitromethane as the internal standard. The yields reported are reproducible to within ±2%. Conversions are calculated based on 1H NMR analysis of the aqueous layer by using DMSO as the internal standard.

Single Step Synthesis of Furan Type Fuel Such as DMTHF from Hexoses Such as Fructose Generally, single step synthesis of furan type fuels such as DMTHF from hexoses such as fructose entails forming a mixture of a hexose, water and acid optionally with an aromatic solvent and metal catalyst. The mixture is reacted at about 25° C. to about 200° C., preferably about 50° C. to about 140° C. under hydrogen at a pressure of about 30 PSI to about 500 PSI, preferably about 300 PSI for about 1 h to about 16 h, preferably about 2 h to about 6 h.

Examples 1 to 13 show conversion of aqueous mixtures that include fructose (pH of 1.0 to −1.0), HI acid and $RhCl_3.xH_2O$ as catalyst under hydrogen atmosphere. The results are shown in Table 1. In examples 1 to 13, the amount of DMTHF is determined by $^1H$ NMR using nitromethane as internal standard.

Example 1

Fructose (1 mmol, 8 wt. % in water), HI (9 mmol, 57 wt. % in water) and $RhCl_3.xH_2O$ (0.1 mmol) are added to a glass reaction vial in open air to form a mixture. The vial containing the mixture then is placed into a bomb, flushed with $H_2$, and charged with 300 PSI $H_2$. The bomb is placed into an oil bath at 25° C. for a period of 6 h to react the mixture to generate DMTHF liquid fuel. Then, 4 ml benzene is added to extract the liquid fuel. The benzene layer having the DMTHF fuel is removed and analyzed to assess the amount of DMTHF present in the reaction product.

Example 2

The procedure of example 1 is employed except that the oil bath has a temperature of 80° C.

Example 3

The procedure of example 1 is employed except that the oil bath has a temperature of 100° C.

Example 4

The procedure of example 1 is employed except that 4 ml benzene is added to the mixture before the reaction and the oil bath has a temperature of 80° C.

Example 5

The procedure of example 1 is employed except that 4 ml benzene and 0.6 g NaCl each are added to the mixture before the reaction and the oil bath has a temperature of 80° C.

Example 6

The procedure of example 1 is employed except that 4 ml toluene is added to the mixture before the reaction and the oil bath has a temperature of 80° C.

Example 7

The procedure of example 1 is employed except that (1 mmol, 6 wt. % fructose in water), 1.5 mmol HI and 4 ml toluene each are added to the mixture and the oil bath has a temperature of 120° C. for 4 h.

Example 8

The procedure of example 1 is employed except that (1 mmol, 6 wt. % fructose in water), 1.2 mmol HI and 4 ml chlorobenzene each are added to the mixture, and the bomb containing the mixture is maintained for 2.5 h in an oil bath that has a temperature of 140° C.

Example 9

The procedure of example 1 is employed except that (1 mmol, 6 wt. % fructose in water), 1.2 mmol HCl is substituted for HI, and 4 ml benzene is added to the mixture and the bomb containing the mixture is maintained for 2 h in an oil bath at temperature of 140° C.

Example 10

The procedure of example 1 is employed except that mmol, 6 wt. % fructose in water), 1.2 mmol HBr is substituted for HI, and 4 ml benzene is added to the mixture and the bomb having the mixture is placed into an oil bath at a temperature of 140° C. for 3 h.

Example 11

The procedure of example 1 is employed except that (1 mmol, 6 wt. % fructose in water), 0.6 mmol $H_2SO_4$ is substituted for HI, and 4 ml benzene is added to the mixture and the bomb having the mixture is placed into an oil bath at a temperature of 140° C. for 2 h to enable reaction of the mixture at 140° C.

Example 12

The procedure of example 1 is employed except that (1 mmol, 10 wt. % fructose in water), 0.05 mmol $RhCl_3.xH_2O$, 1.2 mmol HI and 4 ml chlorobenzene are added to the mixture and the bomb having the mixture is placed into an oil bath at a temperature of 140° C. for 3 h.

Example 13

The procedure of example 1 is employed except that (1 mmol, 20 wt. % fructose in water), 0.01 mmol $RhCl_3.xH_2O$, 1.2 mmol HI, and 4 ml chlorobenzene are added to the mixture and the bomb having the mixture is placed into an oil bath at a temperature of 140° C.

TABLE 1

Synthesis of DMTHF from Fructose in One Step

| EX. | $RhCl_3 \cdot xH_2O$ (mmol) | Temp. (° C.) | Acid (mmol) | Extractant | Time (h) | Yield of DMTHF (%) |
|---|---|---|---|---|---|---|
| 1 | 0.1 | 25 | HI 9 | — | 6 | 0 |
| 2 | 0.1 | 80 | HI 9 | — | 6 | 51 |
| 3 | 0.1 | 100 | HI 9 | — | 6 | 39 |
| 4 | 0.1 | 80 | HI 9 | Benzene | 6 | 81 |
| 5 | 0.1 | 80 | HI 9 | Benzene, NaCl | 6 | 72 |
| 6 | 0.1 | 80 | HI 9 | Toluene | 6 | 78 |
| 7 | 0.1 | 120 | HI 1.5 | Toluene | 4 | 83 |
| 8 | 0.1 | 140 | HI 1.2 | $C_6H_5Cl$ | 2.5 | 85 |
| 9 | 0.1 | 140 | HCl 1.2 | Benzene | 2 | 5 |
| 10 | 0.1 | 140 | HBr 1.2 | Benzene | 3 | 2 |
| 11 | 0.1 | 140 | $H_2SO_4$ 0.6 | Benzene | 2 | 0 |
| 12 | 0.05 | 140 | HI 1.2 | $C_6H_5Cl$ | 3 | 79 |
| 13 | 0.01 | 140 | HI 1.2 | $C_6H_5Cl$ | 3 | 67 |

Separation of Fuel Products and Recycling of Catalyst.

Furan type fuels such as DMTHF may be separated from the aqueous reaction phase by use of organic solvent extractants such as aromatic solvents such as benzene, toluene, chlorobenzene and mixtures thereof; alkane solvents such as isooctane, decane and mixtures thereof; as well as by use of mixtures of aromatic solvents and alkane solvents. However, where the organic solvent also may be used as a liquid fuel, DMTHF need not be separated from the organic solvent. Examples of solvents that may be used as liquid fuels include but are not limited to isooctane, decane and DMTHF.

Advantageously, the $RhCl_3.xH_2O$ catalyst employed in the acidic aqueous reaction mixtures remains active after separation of liquid fuel reaction products. The process therefore may be performed as a continuous process where additional carbohydrates may be continuously added and the process repeated. This is illustrated below by repetition of the reaction process of example 4 for ten reaction cycles. Results of repeated cycling are shown in Table 2.

After each reaction cycle, and upon removal of the benzene extraction layer, an additional 1 mmol fructose and 4 ml benzene are added to the aqueous reaction mixture for use in a subsequent reaction cycle. Yield of DMTHF is determined by $^1H$ NMR using nitromethane as internal standard. The % yields in Table 2 show that a reaction system that includes HI acid and $RhCl_3.xH_2O$ catalyst remains active through at least 10 reaction cycles without little or no reduction in yield. The $^1H$-NMR spectrum of the benzene layer from reaction cycle 3 shows that cis and trans DMTHF isomers are present in a 9:1 ratio.

TABLE 2

Recycling of Catalyst in Fructose Conversion

| Reaction Cycle | 1 | 2 | 3 | 4 | 5 | 6 | 7 | 8 | 9 | 10[a] |
|---|---|---|---|---|---|---|---|---|---|---|
| DMTHF yield (%) | 81 | 91 | 85 | 82 | 85 | 79 | 91 | 86 | 83 | 84 |

[a]The aqueous reaction mixture is filtered and the filtrate used for reaction cycle 10.

Single Step Synthesis of Furan Type Fuel Such as DMTHF from Glucose.

Single step synthesis of furan type fuels such as DMTHF from glucose entails forming a mixture of a hexose, water, acid, metal catalyst and aromatic solvent such as chlorobenzene. The mixture is reacted at a temperature of about 50° C. to about 200° C., preferably about 80° C. to about 160° C., under hydrogen at a pressure of about 30 PSI to about 500 PSI, preferably about 300 PSI for about 4 h to about 20 h, preferably about 16 h. Examples 14 to 19 show conversion of glucose in aqueous solution (pH of about 1.0 to-about 1.0) with HI acid and $RhCl_3 \cdot xH_2O$ as catalyst. The results are shown in Table 3.

Example 14

Glucose (1 mmol, 6 wt. % in water), HI (9 mmol, 57 wt. % in water), $RhCl_3 \cdot xH_2O$ (0.1 mmol), 4 ml chlorobenzene are added to a glass reaction vial in open air to form a mixture. Then the vial is placed into a bomb, flushed with $H_2$, and charged with 300 PSI $H_2$. The bomb is placed into an oil bath at 80° C. for 16 h to react the mixture to generate DMTHF. The chlorobenzene layer that contains DMTHF is analyzed as described above.

Example 15

The procedure of example 14 is employed except that 1.9 mmol HI is used and the oil bath has a temperature of 120° C.

Example 16

The procedure of example 14 is employed except that 1.5 mmol HI is used and the oil bath has a temperature of 140° C.

Example 17

The procedure of example 14 is employed except that 1.2 mmol HI is used and the oil bath has a temperature of 160° C.

Example 18

The procedure of example 14 is employed except that 1.5 mmol HI is used, the oil bath has a temperature of 140° C., and the reaction time is 4 hours.

Example 19

The procedure of example 14 is employed except that 1.5 mmol HI is used, the oil bath has a temperature of 140° C. and the reaction time is 8 hours.

TABLE 3

Synthesis of DMTHF from Conversion of Glucose in One Step

| Ex. | Temp (° C.) | HI (mmol) | Time (h) | DMTHF yield (%) |
|---|---|---|---|---|
| 14 | 80 | 9 | 16 | 4 |
| 15 | 120 | 1.9 | 16 | 64 |
| 16 | 140 | 1.5 | 16 | 74 |
| 17 | 160 | 1.2 | 16 | 71 |
| 18 | 140 | 1.5 | 4 | 46 |
| 19 | 140 | 1.5 | 8 | 58 |

Single Step Synthesis of Furan Derivative Fuel from Biomass Derived Carbohydrates.

Single step synthesis of furan derivative type fuels such as DMTHF from biomass derived carbohydrates such as fructose entails forming a mixture of a biomass derived carbohydrate, water, acid and metal catalyst and aromatic solvent such as chlorobenzene. The mixture is reacted at a temperature of about 80° C. to about 160° C., preferably about 140° C., under hydrogen at a pressure of about 30 PSI to about 500 PSI, preferably about 300 PSI, for about 4 h to about 20 h, preferably about 16 h. Yield is determined by $^1H$ NMR and GC analysis using nitromethane as internal standard. Examples 20 to 25 illustrate synthesis of furan derivatives as liquid fuels from biomass derived carbohydrates. The results are shown in Table 4.

Example 20

Fructose (1 mmol, 6 wt. % in water), HI (1.5 mmol, 57 wt. % in water), $RhCl_3 \cdot xH_2O$ (0.1 mmol), and 4 ml chlorobenzene are added to a glass reaction vial in open air to form a mixture. Then the vial is put into a bomb, flushed with $H_2$, and charged with 300 PSI $H_2$. The bomb is placed into an oil bath at 140° C. for 16 h to react the mixture and to generate a reaction product that includes furan derivatives. The chlorobenzene layer that includes the furan derivative is analyzed as described above. GC-MS analysis of the organic layer shows that DMTHF is the major product and small amounts of C6 reaction side products. The C6 side products include 2,5-dimethylfuran, 2-ethyltetrahydrofuran, 2-methyltetrahydropyran, and tetrahydro-5-methylfuran-2-methanol. The C6 side products may be extracted using the procedure employed to extract fuels such as DMTHF.

Example 21

The procedure of example 20 is employed except that glucose (1 mmol, 6 wt. % in water) is substituted for fructose.

Example 22

The procedure of example 20 is employed except that inulin (1 mmol, 6 wt. % in water) is substituted for fructose.

Example 23

The procedure of example 20 is employed except that Sucrose (1 mmol, 6 wt. % in water) is substituted for fructose.

Example 24

The procedure of example 20 is employed except that cellulose (1 mmol, 6 wt. % in water) is substituted for fructose.

Example 25

The procedure of example 20 is employed except that xylose (1 mmol, 6 wt. % in water) is substituted for fructose.

Example 31

The procedure of example 26 is employed except that Cellulose (0.18 g) is substituted for glucose, 70 μl HCl (0.8

TABLE 4

Transformation Yields of Carbohydrates to Liquid Fuels

| Ex. | | DMTHF | MTHF | 2,5-dimethyl furan | 2-ethyltetra hydrofuran | 2-methyltetra hydropyran | tetrahydro-5-methylfuran-2-methanol | Total Chemical Yield[a] | Conversion[b] |
|---|---|---|---|---|---|---|---|---|---|
| 20 | Fructose | 85% | 0% | 0(%) | 5(%) | 1(%) | 1(%) | 92(%) | 100(%) |
| 21 | Glucose | 74 | 0 | 1 | 5 | 3 | 0 | 83 | 100 |
| 22 | Inulin | 77 | 0 | 0 | 5 | 0 | 1 | 83 | 96 |
| 23 | Sucrose | 86 | 0 | 0 | 4 | 0 | 0 | 90 | 96 |
| 24 | Cellulose | 57 | 0 | 4 | 6 | 1 | 0 | 68 | 90 |
| 25 | Xylose | | 80 | 0 | 0 | 0 | 0 | 80 | 95 |

[a]Sum of DMTHF and C6 reaction side products.
[b]Conversion based on the leftover glucose in aqueous layer using DMSO as internal standard.
an Single Step Synthesis of Furan Type Fuel Such as DMTHF from Cellulose.

Single step synthesis of furan type fuels such as DMTHF from cellulose entails forming a mixture of cellulose, water, and acid preferably with an alkali halide salt, an aromatic solvent and metal catalyst. The mixture is reacted at about 80° C. to about 200° C., preferably about 160° C. about 170° C. under hydrogen at a pressure of about 30 PSI to about 500 PSI, preferably about 300 PSI for about 4 h to about 20 h, preferably about 16 h. Examples 27 to 33 illustrate Single Step Synthesis of DMTHF from Cellulose. Example 26 is a comparative example that illustrates yield of DMTHF from conversion of glucose. The results are shown in Table 5.

Example 26

Glucose (0.18 g, 1 mmol), RhCl$_3$.xH$_2$O (15 mg, 0.07 mmol), water (1.8 ml), HCl (50 μl, 0.57 mmol), NaI (300 mg, 2 mmol), benzene (4 ml) are added to a glass reaction vial in open air to form a mixture. Then the vial is placed into a bomb, flushed with H$_2$, and charged with 300 PSI H$_2$. The bomb then is placed into an oil bath and heated to 160° C. for 16 h to react the mixture at 160° C. The resulting benzene layer that includes DMTHF is removed for analysis.

Example 27

The procedure of example 26 is employed except that Cellulose (0.18 g) is substituted for glucose.

Example 28

The procedure of example 26 is employed except that Cellulose (0.18 g) is substituted for glucose and 70 μl HCl (0.8 mmol) is used and the reaction continues for 18 h.

Example 29

The procedure of example 26 is employed except that Cellulose (0.18 g) is substituted for glucose and 300 mg NaI (2 mmol) is used and the reaction continues for 18 h.

Example 30

The procedure of example 26 is employed except that Cellulose (0.18 g) is substituted for glucose, 70 μl HCl (0.8 mmol), and 300 mg NaI (2 mmol) are used.

mmol), and 300 mg NaI (2 mmol) are used and the reaction is performed at 170° C. for 18 h.

Example 32

The procedure of example 26 is employed except that Cellulose (0.18 g) is substituted for glucose, 70 μl HCl (0.8 mmol), and 300 mg NaI (2 mmol) are used and the reaction time is 3 h.

Example 33

The procedure of example 26 is employed except that Cellulose (0.18 g) is substituted for glucose, 70 μl HCl (0.8 mmol), and 300 mg NaI (2 mmol) are used and the reaction time is 6 h.

TABLE 5

Single Step Synthesis of DMTHF from Cellulose

| Ex. | Biomass | HCl (μl) | NaI (mg) | Temp (° C.) | Time (h) | DMTHF Yield (%)[a] |
|---|---|---|---|---|---|---|
| 26 | Glucose 0.18 g | 50 | 200 | 160 | 16 | 80 |
| 27 | cellulose 0.18 g | 50 | 200 | 160 | 16 | 0 |
| 28 | cellulose 0.18 g | 70 | 200 | 160 | 18 | 57 |
| 29 | cellulose 0.18 g | 50 | 300 | 160 | 18 | 79 |
| 30 | cellulose 0.18 g | 70 | 300 | 160 | 16 | 80 |
| 31 | cellulose 0.18 g | 70 | 300 | 170 | 18 | 68 |
| 32 | cellulose 0.18 g | 70 | 300 | 160 | 3 | 45 |
| 33 | cellulose 0.18 g | 70 | 300 | 160 | 6 | 70 |

[a]Yield of DMTHF is determined by $^1$H NMR using nitromethane as internal standard.

Single Step Production of Furan Type Fuels from Cellulose and Lignocellulosic Biomass.

Single step synthesis of furan type fuels such as MTHF from lignocellulosic biomass entails forming a mixture of a biomass, water and acid, preferably with an alkali halide salt, an aromatic solvent and metal catalyst. The mixture is reacted at about 80° C. to about 200° C., preferably about 160° C. under hydrogen at a pressure of about 30 PSI to about 500 PSI, preferably about 300 PSI for about 4 h to about 20 h, preferably about 16 h. Examples 34 to 35 illustrate Single Step Synthesis of MTHF from cellulose and Lignocellulosic Biomass. The results are shown in Table 6.

Example 34

Cellulose (0.18 g), RhCl$_3$.xH$_2$O (15 mg, 0.07 mmol), water (1.8 ml), HCl (70 μl, 0.8 mmol), NaI (300 mg, 2 mmol), benzene (4 ml) are added to a glass reaction vial in open air to form a mixture. Then the vial is placed into a bomb, flushed with $H_2$, and charged with 300 PSI $H_2$. The bomb then is placed into an oil bath and heated to 160° C. for 16 h to react the mixture. The resulting benzene layer is removed for analysis.

Example 35

The procedure of example 34 is employed except that corn stover (0.18 g) is substituted for cellulose.

TABLE 6

Conversion Results from cellulose and untreated corn stover[a]

| Ex. | Biomass | Conversion DMTHF % | Conversion 2,5-dimethyl Furan % | Conversion 2-ethyltetra Hydrofuran % | Conversion Tetrahydro-5-methylfuran-2-methanol % | Conversion 2-methylcyclo Pentanone % | Conversion MTHF % | Conversion % |
|---|---|---|---|---|---|---|---|---|
| 34 | cellulose | 80 | — | 5 | 2 | — | — | 100 |
| 35 | Corn Stover[a] | 49 | 11 | — | — | 3 | 56 | 100 |

[a]Except for MTHF, yields of DMTHF and other side products are based on glucan present in corn stover (37.4 wt %). Yield of MTHF is based on xylan present in corn stover (21.1 wt %).

In another aspect, solid acids such as phosphotungstic acid may be employed. In this aspect, a hexose, cellulose or combination thereof is mixed with phosphotungstic acid, an alkali halide salt, water, metal catalyst and aromatic solvent to form a mixture. The mixture is reacted under hydrogen at a pressure of about 30 PSI to about 500 PSI, preferably about 300 PSI at about 80° C. to about 200° C., preferably about 140° C. to about 160° C. in the presence of an aromatic solvent for about 4 h to about 20 h, preferably about 6 h to about 16 h. This is illustrated in examples 36-38.

Example 36

Fructose (1 mmol, 10 wt. % in water), $RhCl_3$ (0.1 mmol), $H_3PW_{12}O_{40}$ (0.3 mmol), NaI (2 mmol), $H_2$ (300 PSI), benzene (4 ml) are reacted at 140° C. for 16 h. The yield of 72% DMTHF in the benzene layer is determined by $^1H$ NMR using nitromethane as internal standard.

Example 37

Glucose (1 mmol, 10 wt. % in water), $RhCl_3$ (0.1 mmol), $H_3PW_{12}O_{40}$ (0.3 mmol), NaI (2 mmol), $H_2$ (300 PSI), benzene (4 ml) are reacted at 140° C. for 16 h. The yield of 51% DMTHF in the benzene layer is determined by $^1H$ NMR using nitromethane as internal standard.

Example 38

Cellulose (1 mmol, 10 wt. % in water), $RhCl_3$ (0.1 mmol), $H_3PW_{12}O_{40}$ (0.3 mmol), NaI (2 mmol), $H_2$ (300 PSI), benzene (4 ml) are reacted at 160° C. for 16 h. The yield of 47% DMTHF in the benzene layer is determined by $^1H$ NMR using nitromethane as internal standard.

Conversion of Di- and Polysaccharides Directly into Furan Type Fuel

In another aspect, di-saccharides and polysaccharides are directly converted into fuel such as furan type liquid fuel, as illustrated by examples 39-41. The conversion entails reacting a mixture of a saccharide such as cellobiose, an acid, water, catalyst, aromatic solvent under hydrogen at a pressure of about 30 PSI to about 500 PSI, preferably about 300 PSI at a temperature of about 80° C. to about 200° C., preferably about 140° C. for about 4 h to about 20 h, preferably about 16 h.

Example 39

Cellubiose (1 mmol, 6 wt. % in water), HI (1.5 mmol, 57 wt. % in water), $RhCl_3.xH_2O$ (0.1 mmol), 4 ml benzene are added to a glass reaction vial in open air to form a mixture. Then the vial is put into a bomb, flushed with $H_2$, and charged with 300 PSI $H_2$. The bomb is placed into an oil bath at 140° C. for 16 h. The resulting benzene layer that includes DMTHF liquid fuel is analyzed as described above. The 62% yield of DMTHF is determined by 1HNMR using nitromethane as internal standard.

Example 40

The procedure of example 39 is followed except that 1 mmol of amylose is substituted for cellobiose. The yield of DMTHF is determined to be 42%.

Example 41

The procedure of example 39 is followed except that 1 mmol of starch is substituted for amylose. The yield of DMTHF is determined to be 18%.

Transformation of Hexoses such as Fructose to 5-methylfurfural and Catalyst Recycling.

Synthesis of 5-methylfurfural entails reacting a carbohydrate such as any of hexoses such as but not limited to glucose, fructose, mannose, galactose, sorbose and mixtures thereof, pentoses such as xylose, ribose, arabinose and mixtures thereof; any one or more of di-saccharides, oligo-saccharides, and polysaccharides such as sucrose, cellubiose, amylose, inulin, starch, cellulose, hemi-cellulose, xylan and mixtures thereof with $H_2$ under a pressure of about 30 PSI to about 1000 PSI, preferably about 100 PSI to about 500 PSI, more preferably about 300 PSI, at about 25° C. to about 200° C., preferably about 80° C. to about 160° C., more preferably about 75° C. to about 115° C., and even more preferably about 75° C. to about 90° C. for about 0.5 h to about 44 h, preferably about 0.5 h to about 16 h. The reaction may be performed in the presence of an acid such as HI optionally with an alkali halide salt such as NaCl, NaI and mixtures thereof; HCl optionally with an alkali halide salt such as NaCl, NaI and mixtures thereof; HBr optionally with an alkali halide salt such as NaCl, NaI and $H_2SO_4$ optionally with an alkali halide salt such as NaCl, NaI and mixtures thereof, preferably HI and catalyst. Catalysts that may be employed include but are not limited to $RhCl_2.xH_2O$ (Rh 38.5-45.5%), Pd/C, Ru/C, $RuCl_3$, Rh/C, $NiI_3$, $PdI_3$, $RhI_3$ and $IrCl_3.xH_2O$ or mixtures thereof, preferably $RuCl_3$, Pd/C or mixtures thereof. The amount of catalyst may be about 0.1 equivalent % to about 10 equivalent % based on the amount of the carbohydrate such as hexose, preferably about 1 equivalent % to about 5 equivalent % based on the amount of hexose.

In a preferred aspect, the hexose employed for direct synthesis of 5-methylfurfural is fructose. Conversion of fructose to 5-methylfurfural is illustrated in Scheme 1. In Scheme 1, the temperature of reaction is shown as 90° C. and the reaction time is shown as about 0.5 h to about 1.0 h. It is to be understood, however, that the temperature and reaction times are not so limiting. Accordingly, fructose in a biphasic blend of water and aromatic solvent may be reacted with $H_2$ at a pressure of about 30 PSI to about 1000 PSI, preferably about 100 PSI to about 300 PSI. The amount of water and organic solvent in the biphasic blend may vary such as where water is about 20% to about 80% of the blend, remainder organic solvent. The water may be tap, deionized or distilled water, or blends thereof. The aromatic solvent may be any of benzene, alkyl substituted aromatics such as toluene, halo substituted aromatics such as chlorobenzene, blends of benzene with any one or more of alkyl substituted aromatics such as toluene and halo-substituted aromatics such as chlorobenzene and mixtures thereof. The reaction time is about 0.1 h to about 6 h, preferably about 0.5 h to about 2 h at about 25° C. to about 120° C., preferably about 75° C. to about 90° C. The reaction is performed in the presence of a protic type acid such as HI, HCl, $H_2SO_4$ and mixtures thereof, preferably HI, and a catalyst. The catalyst may be $RuCl_3$, Pd/C or mixtures thereof. Where a blend of aromatic solvents such as a solvent blend of benzene-toluene is employed with water, the amount of benzene may be about 0.1% to 99.9% of the benzene-toluene solvent blend, remainder toluene.

SCHEME 1

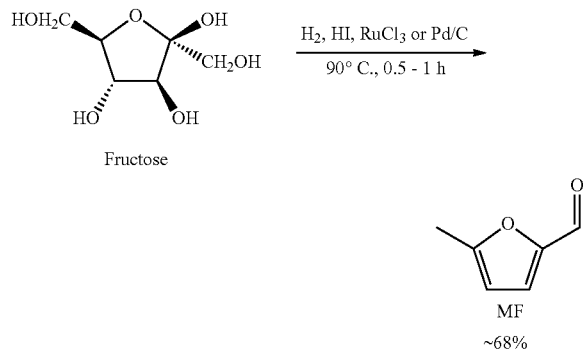

The 5-methylfurfural forms in the organic solvent layer. The 5-methylfurfural may be isolated by separating the organic solvent from the 5-methylfurfural by methods such as distillation or evaporation.

Examples 42-47

Conversion of fructose to 5-methylfurfural. The results are shown in Table 7. Examples 43A, 43B, 46A and 46B illustrate continuous manufacture of 5-methylfurfural.

Example 42

Fructose (1 mmol, 0.18 g), HI (57 wt. % in water, 6 mmol), 5 equiv. % $RuCl_3$, are added to water (1.8 ml) to form a first mixture. This first mixture is added to a glass reaction vial in open air. Benzene (2 ml) then is added to the first mixture to form a second mixture in the vial in open air. The vial with the second mixture then is placed in a high-pressure stainless steel reactor, flushed with $H_2$, and charged with 300 PSI of $H_2$. The reactor then is placed into an oil bath and heated to 75° C. for 2.0 h to form 5-methylfurfural product in the benzene solvent layer. The organic layer containing 5-methylfurfural is separated from the aqueous layer and analyzed by GC and GC-MS.

Example 43

Fructose (1 mmol, 0.18 g), HI (57 wt. % in water, 3 mmol), 5 equiv. % $RuCl_3$, are added to water (1.8 ml) to form a first mixture. This first mixture is added to a glass reaction vial in open air to form a first mixture. Benzene (2 ml) then is added to the first mixture in the vial in open air to form a second mixture. The vial having the second mixture is placed in a high-pressure stainless steel reactor, flushed with $H_2$, and charged with 300 PSI of $H_2$. The reactor then is placed into an oil bath and heated to 90° C. for 1 h to form 5-methylfurfural product in the benzene solvent layer. The benzene layer containing 5-methylfurfural is separated from the aqueous layer and analyzed by GC and GC-MS.

After separation of the benzene layer having 5-methylfurfural therein, 2 ml of the remaining aqueous layer that includes the $RuCl_3$ catalyst and acid is reused by addition of 0.18 gm fructose and 2 ml benzene to the aqueous layer to generate additional 5-methylfurfural product. This enables continuous manufacture of 5-methylfurfural.

Example 43A

Fructose (1 mmol, 0.18 g) is added to the aqueous layer separated from example 43 to form a first mixture. This first mixture is added to a glass reaction vial in open air. Benzene (2 ml) then is added to the first mixture in the vial in open air to form a second mixture. Then the vial is placed in a high-pressure stainless steel reactor, flushed with $H_2$, and charged with 300 PSI of $H_2$. The reactor then is placed in to an oil bath and heated to 90° C. for 1 h to form 5-methylfurfural product in the benzene solvent layer. The benzene layer containing 5-methylfurfural is separated from the aqueous layer and analyzed by GC and GC-MS.

After separation of the benzene layer having 5-methylfurfural therein, 2 ml of the remaining aqueous layer that includes the $RuCl_3$ catalyst and acid is reused by addition of 0.18 gm fructose and 2 ml benzene to the aqueous layer to generate additional 5-methylfurfural product. This enables continuous manufacture of 5-methylfurfural.

Example 43B

Fructose (1 mmol, 0.18 g) is added to the aqueous layer separated from example 43A to form a first mixture. This first mixture is added to a glass reaction vial in open air. Benzene (2 ml) then is added to the first mixture in the vial in open air to form a second mixture. Then the vial having the second mixture is placed in a high-pressure stainless steel reactor, flushed with $H_2$, and charged with 300 PSI of $H_2$. The reactor then is put in to an oil bath and heated to 90° C. for 1 h to form 5-methylfurfural product in the benzene solvent layer. The benzene layer containing 5-methylfurfural is separated from the aqueous layer and analyzed by GC and GC-MS.

Example 44

Fructose (1 mmol, 0.18 g), HI (57 wt. % in water, 6 mmol), 5 equiv. % Pd/C relative to fructose are added to water (1.8 ml) to form a first mixture. This first mixture is added to a glass reaction vial in open air. Benzene (2 ml) then is added to the first mixture in the vial in open air to form a second mixture. Then the vial having the second mixture is placed in a high-pressure stainless steel reactor, flushed with $H_2$, and charged with 300 PSI of $H_2$. The reactor then is placed in to an oil bath and heated to 75° C. for 2.0 h to form 5-methylfurfural product in the benzene solvent layer. The benzene layer containing 5-methylfurfural is separated from the aqueous layer and analyzed by GC and GC-MS.

Example 45

Fructose (1 mmol, 0.18 g), HI (57 wt. % in water, 6 mmol), 1 equiv. % Pd/C relative to fructose are added to water (1.8 ml) to form a first mixture. This first mixture is added to a glass reaction vial in open air. Benzene (2 ml) then is added to the first mixture in the vial in open air to form a second mixture. The vial having the second mixture then is placed in a high-pressure stainless steel reactor, flushed with $H_2$, and charged with 300 PSI of $H_2$. The reactor then is placed in to an oil bath and heated to 75° C. for 2.0 h to form 5-methylfurfural product in the benzene solvent layer. The benzene layer containing 5-methylfurfural is separated from the aqueous layer and analyzed by GC and GC-MS.

Example 46

Fructose (1 mmol, 0.18 g), HI (57 wt. % in water, 3 mmol), 1 equiv. % Pd/C relative to fructose are added to water (1.8 ml) to form a first mixture. This first mixture is added to a glass reaction vial in open air. Benzene (2 ml) then is added to the first mixture in the vial in open air to form a second mixture. Then the vial having the second mixture is placed in a high-pressure stainless steel reactor, flushed with $H_2$, and charged with 300 PSI of $H_2$. The reactor then is placed in an oil bath and heated to 90° C. for 0.5 h to form 5-methylfurfural product in the benzene solvent layer. The benzene layer containing 5-methylfurfural is separated from the aqueous layer and analyzed by GC and GC-MS.

After separation of the benzene layer having 5-methylfurfural therein, 2 ml of the remaining aqueous layer that includes the $RuCl_3$ catalyst and acid is reused by addition of 0.18 gm fructose and 2 ml benzene to generate additional 5-methylfurfural product. This enables continuous manufacture of 5-methylfurfural.

Example 46A

Fructose (1 mmol, 0.18 g), HI (57 wt. % in water, 3 mmol), 1 equiv. % relative to fructose of the recycled Pd/C catalyst from example 46 are added to water (1.8 ml) to form a first mixture. This first mixture is added to a glass reaction vial in open air. Benzene (2 ml) then is added to the first mixture in the vial in open air. Then the vial is placed in a high-pressure stainless steel reactor, flushed with $H_2$, and charged with 300 PSI of $H_2$. The reactor then is placed in to an oil bath and heated to 90° C. for 0.5 h to form 5-methylfurfural product in the benzene solvent layer. The benzene layer containing 5-methylfurfural is separated from the aqueous layer and analyzed by GC and GC-MS.

After separation of the benzene layer having 5-methylfurfural therein, 2 ml of the remaining aqueous layer that includes the $RuCl_3$ catalyst and acid is reused by addition of 0.18 gm fructose and 2 ml benzene to generate additional 5-methylfurfural product. This enables continuous manufacture of 5-methylfurfural.

Example 46B

Fructose (1 mmol, 0.18 g) is added to the aqueous layer separated from example 46A to form a first mixture. This first mixture is added to a glass reaction vial in open air. Benzene (2 ml) then is added to the first mixture in the vial in open air. Then the vial is placed in a high-pressure stainless steel reactor, flushed with $H_2$, and charged with 300 PSI of $H_2$. The reactor then is placed in to an oil bath and heated to 90° C. for 0.5 h to form 5-methylfurfural product in the benzene solvent layer. The benzene layer containing 5-methylfurfural is separated from the aqueous layer and analyzed by GC and GC-MS.

Example 47

Fructose (1 mmol, 0.18 g), HI (57 wt. % in water, 3 mmol), 1 equiv. % Pd/C relative to fructose are added to water (1.8 ml) to form a first mixture that is added to a glass reaction vial in open air. Then the vial is placed in a high-pressure stainless steel reactor, flushed with $H_2$, and charged with 100 PSI of $H_2$. The reactor then is placed in to an oil bath and heated to 90° C. for 1 h to form 5-methylfurfural product in the benzene solvent layer. The organic layer containing 5-methylfurfural is separated from the aqueous layer and analyzed by GC and GC-MS.

TABLE 7

Catalytic conversion of fructose to 5-methylfurfural[a]

| Ex. | Catalyst | HI | Temp. | Time | Yield | Conversion of fructose |
|---|---|---|---|---|---|---|
| 42 | $RuCl_3$ 5(Equiv. %) | 6 mmol | 75° C. | 2 h | 67% | 98% |
| 43 | $RuCl_3$ 5 | 3 | 90 | 1 | 64 | 97 |
| 43A[b] | $RuCl_3$ 5 | 3 | 90 | 1 | 63 | 98 |
| 43B[c] | $RuCl_3$ 5 | 3 | 90 | 1 | 63 | 97 |
| 44 | Pd/C 5 | 6 | 75 | 2 | 63 | 95 |
| 45 | Pd/C 1 | 6 | 75 | 2 | 63 | 94 |
| 46 | Pd/C 1 | 3 | 90 | 0.5 | 68 | 97 |
| 46A[d] | Pd/C 1 | 3 | 90 | 1 | 69 | 95 |
| 46B[e] | Pd/C 1 | 3 | 90 | 1 | 68 | 95 |
| 47[f] | Pd/C 1 | 3 | 90 | 1 | 59 | 93 |

[a]Conditions: Fructose, 1 mmol; HI, 57% in water; $H_2$, 300 PSI; $H_2O$, 1.8 ml; benzene, 2 ml.
[b]The catalyst is recycled from example 43;
[c]The catalyst is recycled from example 43A;
[d]The catalyst is recycled from example 46;
[e]The catalyst is recycled from example 46A
[f]100 PSI $H_2$ Examples 48-51 illustrate conversion of carbohydrate-based biomass to 5-methylfurfural. The results are shown in Table 8.

Example 48

Inulin (1 mmol), HI (57 wt. % in water, 6 mmol), 5 equiv. % $RuCl_3$ relative to inulin, water (1.8 ml) and benzene (4 ml) are added to a glass reaction vial in open air. Then the vial is placed in a high-pressure stainless steel reactor, flushed with $H_2$, and charged with 300 PSI of $H_2$. The reactor then is placed in an oil bath and heated to 75° C. for 2 h to form 5-methylfurfural product in the benzene solvent layer. The benzene layer containing 5-methylfurfural is separated from the aqueous layer and analyzed by GC and GC-MS.

Example 49

Sucrose (1 mmol), HI (57 wt. % in water, 6 mmol), 5 equiv. % $RuCl_3$ relative to sucrose, water (1.8 ml) and benzene (4 ml) are added to a glass reaction vial in open air. Then the vial is placed in a high-pressure stainless steel reactor, flushed with $H_2$, and charged with 300 PSI of $H_2$. The reactor then is placed in an oil bath and heated to 75° C. for 2 h to form 5-methylfurfural product in the benzene solvent layer. The benzene layer containing 5-methylfurfural is separated from the aqueous layer and analyzed by GC and GC-MS.

Example 50

Glucose (1 mmol), HI (57 wt. % in water, 3 mmol), 1 equiv. % Pd/C relative to glucose, water (1.8 ml), and benzene (4 ml) are added to a glass reaction vial in open air. Then the vial is placed in a high-pressure stainless steel reactor, flushed with $H_2$, and charged with 300 PSI of $H_2$. The reactor then is placed in to an oil bath and heated to 105° C. for 2 h to form 5-methylfurfural product in the benzene solvent layer. The benzene layer containing 5-methylfurfural is separated from the aqueous layer and analyzed by GC and GC-MS.

Example 51

Cellulose (1 mmol), HI (57 wt. % in water, 0.1 mmol), NaI (1 mmol), 1 equiv. % Pd/C relative to Cellulose, water (1.8 ml), and benzene (4 ml) are added to a glass reaction vial in open air. Then the vial is placed in a high-pressure stainless steel reactor, flushed with $H_2$, and charged with 300 PSI of $H_2$. The reactor then is placed in to an oil bath and heated to 115° C. for 2 h to form 5-methylfurfural product in the benzene solvent layer. The benzene layer containing 5-methylfurfural is separated from the aqueous layer and analyzed by GC and GC-MS.

The invention claimed is:

1. A method for manufacture of 5-methylfurfural comprising,
   reacting a mixture of reactants comprising a carbohydrate selected from the group consisting of hexoses, pentoses, polysaccharides and mixtures thereof, water, organic solvent and a catalyst selected from the group consisting of $RhCl_3.xH_2O$ (Rh 38.5-45.5%), Pd/C, Ru/C, $RuCl_3$, Rh/C, $NiI_3$, $PdI_3$, $RhI_3$ and $IrCl_3.xH_2O$ and mixtures thereof, an acid selected from the group consisting of HI, HCl, HBr, $H_2SO_4$ and mixtures thereof, and
   in the presence hydrogen pressure of about 30 PSI to about 1000 PSI at about 25° C. to about 200° C. for about 0.5 h to about 44 h to form 5-methylfurfural product in the absence of further processing steps.

2. The method of claim 1 wherein the carbohydrate is a hexose.

3. The method of claim 2 wherein the hexose is fructose.

4. The method of claim 2 wherein the acid is HI.

5. The method of claim 2 wherein the catalyst is any one or more of $RuCl_3$ and Pd/C.

6. The method of claim 5 wherein the organic solvent is any one or more of an aromatic solvent is selected from the group consisting of benzene, toluene, chlorobenzene and mixtures thereof, an alkane solvent selected from the group consisting of isooctane, decane and mixtures thereof, and mixtures of alkanes and aromatics.

7. A method of manufacture of 5-methylfurfural comprising forming a reaction mixture of fructose, HI, catalyst, water and benzene, and reacting the mixture under hydrogen pressure of about 300 PSI at about 75° C. to about 90° C. for about 2 h to produce 5-methylfurfural in the absence of further processing steps.

8. The method of claim 7 wherein the catalyst is $RuCl_3$.

9. The method of claim 7 wherein the catalyst is Pd/C.

10. A method of manufacture of 5-methylfurfural comprising forming a reaction mixture of a carbohydrate selected from the group consisting of inulin, sucrose, glucose, cellulose or mixtures thereof, HI, $RuCl_3$, water and benzene, and reacting the mixture under hydrogen pressure of about 300 PSI at about 75° C. for about 2 h to produce 5-methylfurfural in the absence of further processing steps.

11. The method of claim 10 wherein the carbohydrate is fructose.

12. The method of claim 1 wherein the carbohydrate is glucose.

13. The method of claim 1 wherein the carbohydrate is sucrose.

14. The method of claim 1 wherein the carbohydrate is cellulose.

15. A method for continuous manufacture of 5-methylfurfural comprising,
   Step 1. forming a reactant mixture comprising a carbohydrate selected from the group consisting of hexoses,

TABLE 8

Catalytic conversion of carbohydrate-based biomass to 5-methylfurfural[a]

| Ex. | Catalyst | HI | Temp. | Time | Yield | Conversion |
|---|---|---|---|---|---|---|
| 48 | $RuCl_3$ 5(Equiv. %) | 6 mmol | 75° C. | 2 hr | 61% | 96% |
| 49 | $RuCl_3$ 5(Equiv. %) | 6 | 75 | 2 | 35 | 45 |
| 50 | Pd/C 1(Equiv. %) | 3 | 105 | 2 | 31 | 81 |
| 51 | Pd/C 1(Equiv. %) | 0.1 + NaI (1 mmol) | 115 | 2 | 42 | |

[a]Conditions: Carbohydrate, 1 mmol; Catalysts, 1% or 5 equiv. % relative to carbohydrate; HI, 57% in water; H2, 300 PSI; H2O, 1.8 ml; benzene, 4 ml, 2 h.

pentoses, polysaccharides, and mixtures thereof, water, an organic solvent and a catalyst selected from the group consisting of $RhCl_3 \cdot xH_2O$ (Rh 38.5-45.5%), Pd/C, Ru/C, $RuCl_3$, Rh/C, $NiI_3$, $PdI_3$, $RhI_3$ and $IrCl_3 \cdot xH_2O$ or mixtures thereof, an acid selected from the group consisting of HI, HCl, HBr, $H_2SO_4$ and mixtures thereof, and Step 2. reacting the mixture under hydrogen pressure of about 30 PSI to about 1000 PSI at about 25° C. to about 200° C. for about 0.5 h to about 44 h to form a reaction product having 5-methylfurfural, Step 3. separating the 5-methylfurfural from the reaction product to form an aqueous portion having catalyst and acid, combining the aqueous portion with additional carbohydrate and aromatic solvent, and repeating steps 2 and 3 in the absence of further processing steps.

* * * * *